United States Patent [19]

Szegö et al.

[11] Patent Number: 4,486,595

[45] Date of Patent: Dec. 4, 1984

[54] PROCESS FOR THE PREPARATION OF STABLE AQUEOUS SUSPENSIONS OF METHYL N-(2-BENZIMIDZOLYL)-CARBAMATE

[75] Inventors: András Szegö ; Ferenc Kováts; Viktória Péterdi; István Bóné ; László Gombos; Ferenc Öz, all of Budapest; Imre Símon, Visegrád, all of Hungary

[73] Assignee: Chinoin Gyogyszer Es Vegyeszeti Termekek Gyara R.T., Budapest, Hungary

[21] Appl. No.: 543,807

[22] Filed: Oct. 24, 1983

Related U.S. Application Data

[63] Continuation of Ser. No. 260,161, May 4, 1981, abandoned.

[30] Foreign Application Priority Data

May 9, 1980 [HU] Hungary .............................. 1142/80

[51] Int. Cl.$^3$ ............................................ C07D 235/32
[52] U.S. Cl. .................................. 548/306; 424/273 R
[58] Field of Search ..................... 548/306; 424/273 R

[56] References Cited

FOREIGN PATENT DOCUMENTS 1195180  6/1970  United Kingdom ................ 548/306

*Primary Examiner*—Richard A. Schwartz
*Attorney, Agent, or Firm*—Karl F. Ross

[57] ABSTRACT

The invention relates to a new process for the preparation of stable aqueous suspensions of methyl N-(2-benzimidazolyl)carbamate. According to the invention an aqueous solution of an addition salt of methyl N-(2-benzimidazolyl)carbamate and an inorganic acid, optionally containing an excess amount of acid is reacted with an aqueous potassium, sodium or ammonium hydroxide solution or ammonia gas, in the presence of a wetting, dispersing and antifoaming agent and optionally of a protecting colloid at a temperature of 50° C. to 100° C., and if desired, the suspension obtained is concentrated or diluted. The suspension prepared by this process can either be used directly or can be supplemented with further additive(s) conventionally used in the preparation of plant protecting agents.

10 Claims, No Drawings

PROCESS FOR THE PREPARATION OF STABLE AQUEOUS SUSPENSIONS OF METHYL N-(2-BENZIMIDZOLYL)-CARBAMATE

This application is a continuation of application Ser. No. 260,161 filed May 4, 1981, now abandoned.

The invention relates to a process for the preparation of stable aqueous suspensions of methyl N-(2-benzimidazolyl)-carbamate. More particularly, the invention concerns a process for the preparation of stable aqueous suspensions containing 10 to 50% by weight of methyl-N-(2-benzimidazolyl)-carbamate (also referred to herein as carbendazime).

According to the invention a desired stable aqueous suspension is prepared by reacting an aqueous solution of an addition salt of carbendazime and an inorganic acid, optionally containing an excess amount of acid, with an aqueous potassium, sodium or ammonium hydroxide solution or ammonia gas, in the presence of a wetting, dispersing and antifoaming agent and optionally a protecting colloid, at a temperature of 50° C. to 100° C. and if desired, concentrating or diluting the suspension obtained, which can be used also directly, in a manner known per se and/or admixing same with further additive(s) conventionally used in the preparation of plant protecting compositions.

Carbendazime is a well known fungicidally active compound.

Of the numerous plant protecting formulations stable suspensions have many advantages (i.e. they are easy to dilute, are not dust-producing, due to their small grain size can economically be used, etc.) and therefore their application is gaining increasingly importance. Naturally aqueous suspensions could most advantageously be used. Their application is, however, strongly limited by the fact that the preparation of suspensions with a small grain size which are stable even after dilution is rather cumbersome and expensive. To obtain stable suspensions the grain size of the active ingredient has to be reduced, preferably below 5 microns. The reduction in size is generally performed by a so called superfine grinding, which can be carried out only in expensive equipment and has a high energy demand.

Following the process according to the invention stable aqueous suspensions of carbendazime can be prepared by a very simple technology, without grinding and if desired, the compositions obtained can directly be put onto the market.

We have surprisingly found that appropriately selected wetting, dispersing and antifoaming agents and optionally protecting colloids ensure not only the desired properties of a ready suspension in a known manner but they also inhibit the formation of larger particles during the precipitation of carbendazime from an acid solution. The size of the grains obtained in this way is below 5 microns.

According to a preferred embodiment of the invention an aqueous solution of an acid addition salt of carbendazime with hydrochloric acid and/or phosphoric acid is used as a starting mixture. Carbendazime is preferably precipitated by an ammonium hydroxide solution or ammonia gas. One or more of the following dispersing and/or wetting agents can preferably be employed: alkylligninsulfonates, oxylignines, urea, naphthalensulfonic acid-Na-formaldehyd, alkylpolyglycol ether sulfonates, alkyl ether sulfonates, alkylphenolpolyglycol ethers, dialkylsulfosuccinates, ethoxylated and hydrogenated castor oil, fatty alcohol polyglycol ethers, oxyethylenoxypropylen condensates, phosphated alkylaryl-Ca salts, alkylarylsulfonate-Ca salts, semiester-sulfonsuccinates. Urea, ligninsulfonates and alkylphenylpolyglycol ethers and ethoxylated castor oil, ethoxylated alkylaryl-Ca sulfonates and phosphotates and their mixtures.

As protecting colloids one or more of the following protecting colloids having a low degree of polymerization and a low viscosity can preferably be used: carboxymethyl cellulose, carboxymethyl-starch Na-salt, methylhydroxyethyl cellulose, preferably hydroxyethyl cellulose, polyvinylalcohol, polyvinylpyrrolidone. Protecting colloids in a collodial system become connected with the solid phase and inhibit agglomeration.

Of the antifoaming agents preferably alkyl silicates, e.g. methyl silicates as well as mineral and vegetable oils can be used, and also have a soil improving activity.

In addition to the above ingredients also further additives can be present when precipitating carbendazime. Such additives include polybasic alcohols as evaporation decreasing agents, e.g. ethylene or propylene glycol or glycerine; various silicates or bentonite for loosening the precipitate, polysaccharides as antideposit agents, adjuvants, e.g. dimethyl formamide, dimethyl sulfoxide. The latter additives are not required for the preparation of a suspension containing grains in an appropriate size, they rather improve the properties of the ready for use formulations in a known manner.

The dispersing, wetting and antifoam agents, optionally protecting colloids and if desired, further additives can be present in the acid solution of carbendazime or in the alkaline solution used for neutralization or in both.

According to the invention an acid solution of carbendazime, optionally containing additives, is poured into the alkaline solution, optionally containing the above-listed additives with stirring, or the solutions are admixed in a reverse order or they are contacted continuously. By a proper selection of the quantity of the base employed the pH of the suspension obtained is adjusted to 4 to 9.

The compositions prepared according to the invention contain 10 to 50% by weight, preferably 20 to 40% by weight of carbendazime. The compositions obtained can directly be put to the market but if desired, can be concentrated in a known manner or can be supplemented by further additives listed above.

The compositions prepared according to the invention preferably have the following percentage composition:

| | |
|---|---|
| carbendazime | 20 to 40% by weight |
| inorganic salt (formed during neutralization of an acid solution of carbendazime) | 3 to 15% by weight |
| dispersing agent | 2 to 15% by weight |
| wetting agent | 1 to 4% by weight |
| protecting colloids | 0 to 4% by weight |
| antifoaming agent | 1 to 4% by weight |
| evaporation reducing agent | 0 to 5% by weight |
| precipitate loosening and antisediment agent | 0 to 4% by weight |
| adjuvant | 0 to 3% by weight |
| water | 9 to 73% by weight |

Further details of the invention are illustrated by the following, non-limiting Examples. In all of the Examples the grain size of carbendazime is below 5 microns.

EXAMPLE 1

In a conventional laboratory apparatus equipped with a stirrer (60 r.p.m.) 1.6 g. of polyvinyl pyrrolidone ("Plasdone K 15"), 3 g. of urea, 1 g. of polyvinyl alcohol ("Polyciol M 13/140"), 1.5 g. of alkylphenolpolyglycol ether ("Tenzilin 080") and 4 g. of methyl silicone oil ("Szilorol M") are dissolved in 139 g. of a 14.8% aqueous hydrochloric acid solution.

To the mixture 80 g. of carbendazime are added at 80° to 90° C. at 60 r.p.m. and the temperature is kept at this level until total dissolution. To the solution 42 g. of a 23% aqueous ammonium hydroxide solution are added in 3 minutes, with stirring. The ammonium hydroxide solution contains 0.5 g. of ethoxylated and hydrogenated castor oil ("Chromophor RH 40").

The composition obtained contains carbendazime having a grain size below 5 μm in a concentration of 29.4%.

EXAMPLE 2

In an aqueous solution containing 139 g. of a 14.8% hydrochloric acid solution and 5.7% phosphoric acid solution the additives given in Example 1 and carbendazime are dissolved. The solution is neutralized as described in Example 1 with 60 g. of a 23% aqueous ammonium hydroxide solution.

EXAMPLE 3

The product according to Example 1 is homogenized with 4.5 g. of ethoxylated and hydrogenated castor oil ("Chromophor KH 40"), 8 g. of glycerine, 6 g. of urea and 7.2 g of polyvinyl alcohol ("Polyviol M 13/140").

EXAMPLE 4

To the product of Example 2 the additives according to Example 3 are given.

EXAMPLE 5

To the product of Example 3 instead of 4.5 g. of ethoxylated and hydrogenated castor oil ("Chromophor RH 40") an equivalent amount of alkylphenol polyglycol ether ("Tenzilin 080") is added.

EXAMPLE 6

To the product of Example 2 the additives according to Example 5 are given.

EXAMPLE 7

To the product of Example 1 6 g. of ethoxylated and hydrogenated castor oil ("Chromophor RH 40"), 9 g. of urea, 12 g. of synthetic silicic acid, 12 g. of glycerine, 3 g. of carboxymethyl starch-Na and 3 g. of dialkyl sulfosuccinate ("Aerosol OT 100") are added.

EXAMPLE 8

To the product of Example 2 3 g. of alkyl polyglycolether sulfate sodium ("Evidet 27"), 9 g. of urea, 6 g. of synthetic silicic acid, 6 g. of glycerine, 3 g. of carboxymethyl starch-Na and 3 g. of dialkyl sulfosuccinate ("Aerosol OT 100") are added.

EXAMPLE 9

The products of Examples 7 and 8 are supplemented with 6 g. of dimethyl formamide.

EXAMPLE 10

In 139 g. of a 14.8% aqueous hydrochloric acid solution 1 g. of polyvinyl pyrrolidone ("Plastone K 15"), 2 g. of alkylphenol polyglycol ether ("Tenzilin 0807") and 4 g. of methyl silicone oil ("Szilorol M") are dissolved, followed by the dissolution of 103 g. of carbendazime at 80°–90° C., with stirring (60 r.p.m.). 10 g. of ammonia gas are introduced into the solution. A composition containing 89.8% of carbendazime is obtained, and the grain size of carbendazime is below 5 μm.

EXAMPLE 11

The product of Example 10 is supplemented by the additives according to Examples 7, 8 and 9, respectively.

EXAMPLE 12

In a conventional laboratory apparatus equipped with a stirrer (60 r.p.m.) 145 g. of a 14.1% aqueous hydrochloric acid solution are heated up to 90° C., 100 g. of carbendazime are added and are dissolved, while the temperature is kept constant. 12.5 g. of alkylphenol polyglycol ether ("Tenzilidin 080") are added to the solution. A mixture of 58.6 g. of a 16.8% aqueous ammonium hydroxide solution, 10.1 g. of pharmaceutical white oil, 1.1 g. of fatty alcohol polyglycol ether ("Emulsogen M") is prepared. The mixture is then added to the carbendazime solution with stirring, in one minute. The suspension is cooled to 60° C., whereupon a solution of 0.9 g. of polysaccharide ("Tensiofix 821") in 26.4 g. of ethylene glycol and 14.3 g. of water is added and after 15 minutes of stirring the suspension is cooled to 40° C. The suspension formed contains 27.1% of carbondazime, which has a grain size less than 5 μm.

EXAMPLE 13

To the product of Example 12 a mixture of 3.8 g. of oxyethylene-oxypropylene alkyl-phenol condensate and alkylaryl sulfonate calcium mixture ("Tensiofix B 7425") and 3.8 g. of alkylphenol polyglycol ether sulfonate ("Tensiofix DP 24") is added. Tensides are admixed by a conventional homogenization process and 0.8 g. of an antifoaming agent ("Tensiofix L 051") are added. The flotability of the suspension according to WHO standard amounts to 98%.

EXAMPLE 14

In the process according to Example 13 instead of surface active agents a tenside containing 3.8 g. of Tensiofix B 7425 and 3.8 g. of phosphated and non-ionic part ("Tensiofix CG 21") is employed. The properties of the product are identical with the properties of the formulation obtained in Example 13.

EXAMPLE 15

To the product obtained in Example 12 7.6 g. of Tensiofix DP 24 are added and the mixture is supplemented with 0.8 g. of an antifoaming agent after homogenization. The properties of the product are identical with the properties of the product of Example 13.

EXAMPLE 16

In place of the tenside used in Example 15 7.6 g. of semiester sulfosuccinate ("Tensiofix H 925) are employed.

EXAMPLE 17

To the product of Example 12 3.8 g. of calcium alkylaryl sulfonate ("Atlox 4852 B") and 3.8 g. of a mixture of calcium alkylaryl sulfonate and a non-ionic tenside ("Atlex 3387 BM") are added. After homogenisation 0.8 g. of Tensiofix L 051 are added as an antifoaming agent. The flotability of the end product is 95%.

BIOLOGICAL TESTS

EXAMPLE 1

The effect of ammonium chloride containing fungicides, comprising carbendazime as active ingredient on the germination of wheat, mustard, Italian millet (setaria italica) and tomato seeds:

In a Petri dish having a diameter of 9.5 cm tomato, mustard, Italian millet and wheat seeds were germinated between two wet filter papers. In to each Petri dish 50 wheat seeds and 100 tomato, 100 mustard and 100 Italian millet seeds, resp. were placed. On to the seeds 1 mg/Petri dish, 5 mg/Petri dish and 10 mg/Petri dish formulated test substances were dropped by a micropipette, in a dose of 3 ml/Petri dish. The seeds were then covered with another wet filter paper and the Petri dishes were kept in a thermostate at 24° C. The filter paper covering the seeds was wetted by 2 ml. of water every day. The germination was evaluated one week after the treatment.

During the evaluation the ungerminated seeds and the visually deformed seedlings were counted and their number was related to the results obtained in connection with untreated control. The tests were carried out in four repetitions.

| Treatment | Test plants | | | | | | | |
|---|---|---|---|---|---|---|---|---|
| | wheat | | Italian millet | | tomato | | mustard | |
| | G[%] | F | G[%] | F | G[%] | F | G[%] | F |
| untreated control | 95 | 0 | 90 | 0 | 89 | 0 | 98 | 0 |
| ABEM 25 FW | | | | | | | | |
| 1 mg | 95 | 0 | 89 | 0 | 90 | 1 | 94 | 0 |
| 5 mg | 96 | 0 | 90 | 0 | 89 | 0 | 100 | 0 |
| 10 mg | 94 | 2 | 90 | 0 | 88 | 0 | 99 | 0 |
| ABEM 50 FW | | | | | | | | |
| 1 mg | 96 | 0 | 92 | 0 | 90 | 2 | 100 | 1 |
| 5 mg | 94 | 1 | 90 | 0 | 92 | 1 | 98 | 3 |
| 10 mg | 95 | 2 | 89 | 0 | 89 | 3 | 95 | 3 |

G[%] = germination %;
F = phytotoxicity;

| ABEM 25 FW: | carbendazime | 25% by weight |
|---|---|---|
| | lignine sulfonate-Na | 3% by weight |
| | Na—alkylether sulfate | 2% by weight |
| | hydroxyethylcellulose | 1% by weight |
| | water | ad 100% by weight |
| ABEM 50 FW: | carbendazime | 25% by weight |
| | NH4Cl | 21% by weight |
| | lignine sulfonate-Na | 3% by weight |
| | Na—alkylether sulfate | 2% by weight |
| | hydroxyethlylcellulose | 1% by weight |
| | water | ad 100% by weight |

The amounts of the test formulations as indicated in the Table relate to one Petri dish.

EXAMPLE 2

Phytotoxicity of various formulations prepared according to the invention.

In a cultivation pot having an area of 228 cm² wheat, mustard, tomato and Italian millet plants were cultivated. For this purpose 200 seeds of mustard, tomato and Italian millet, resp. and 100 seeds of wheat were sown per pot.

After 10 days the test plants were treated with 2.5 kg./ha., 5 kg./ha. and 10 kg./ha., resp. of the test formulations by spraying a corresponding tank mixture in an amount of 500 lit./ha. The phytotoxic effect of the test formulations was examined one week after the treatment by visual observation of the plants treated. The obtained results are listed in the following Table.

| Treatment | Dose [kg/ha] | Test plants | | | | | | | | | | | |
|---|---|---|---|---|---|---|---|---|---|---|---|---|---|
| | | wheat | | | tomato | | | Italian millet | | | mustard | | |
| | | A | B | C | A | B | C | A | B | C | A | B | C |
| untreated control | | 0 | 0 | 0 | 0 | 0 | 0 | 0 | 0 | 0 | 0 | 0 | 0 |
| Example 14 | 2.5 | 0 | 0 | 0 | 0· | 0 | 0 | 0 | 0 | 0 | 0 | 0 | 0 |
| | 5.0 | 0 | 0 | 0 | 00 | 0 | 0 | 0 | 0 | 0 | 0 | 0 | |
| | 10.0 | 0 | 0 | 0 | 0 | 0 | 0 | 0 | 0 | 0 | 0–1 | 0 | 0 |
| ABEM 50 FW | 2.5 | 0 | 0 | 0 | 0 | 0 | 0 | 0 | 0 | 0 | 0 | 0 | 0 |
| | 5.0 | 0 | 0 | 0 | 0 | 0 | 0 | 0 | 0 | 0 | 0 | 0–1 | 0 |
| | 10.0 | 0 | 0 | 0 | 0–1 | 0 | 0 | 0–1 | 0 | 0 | 1 | 1 | 0 |

The phytotoxic effect was evaluated on the basis of the following scale:

0 = there is no abnormality in color, growth or shape, the plants have the same appearance as the control plants 1 = the leaves show a slight discoloration, in growth and shape no difference from the control can be observed 2 = on the leaves brown spots having a diameter of 1 to 2 mm. are observed, the edge of the leaves is withered, and a malformation of leaves is observed 3 = at least 50% of the leaves shows a brown discoloration, a malformation of leaves and growth inhibition can be observed 4 = the leaves are decayed, defoliation takes place and the whole plant is decayed A = shape of the leaves
B = discoloration
C = growth irregularity.

EXAMPLE 3

Phytotoxicity of various formulations prepared according to the invention—field trial:

Into 25 m² microplots (5 m×5 m) winter wheat and winter barley was sown. From the winter wheat 380 kg./ha., from the winter barley 150 kg./ha. were used. Prior to sowing pea for canning industry was cultivated on the same plots. No weed killing was carried out. The test were performed in four repetitions.

During the cultivation period the test plants were treated with the formulations to be tested three times. The first treatment was performed 1 month after sowing, the second one when the plants are stooling and the third one during blooming. Each time 1.0 kg./ha., 1.5 kg./ha. and 2.0 kg./ha. formulations were applied in the form of tank mixtures, in an amount of 80 lit./ha to 80 lit./ha. The treatment was carried out by spraying. Phytotoxicity was evaluated as described in Example 2 each time one week after treatment. The results obtained are indicated in the following Table.

|  |  | Test plants (phytotoxicity) | | | | | | | | | | | | | | | | |
|---|---|---|---|---|---|---|---|---|---|---|---|---|---|---|---|---|---|---|
|  |  | winter wheat | | | | | | | | winter barley | | | | | | | | |
|  |  | 1. | | | 2. | | | 3. | | | 1. | | | 2. | | | 3. | | |
| Treatment | Dose [kg/ha] | A | B | C | A | B | C | A | B | C | A | B | C | A | B | C | A | B | C |
| untreated control | | 0 | 0 | 0 | 0 | 0 | 0 | 0 | 0 | 0 | 0 | 0 | 0 | 0 | 0 | 0 | 0 | 0 | 0 |
| ABEM 25 FW (contr.) | 1.0 | 0 | 0 | 0 | 0 | 0 | 0 | 0 | 0 | 0 | 0 | 0 | 0 | 0 | 0 | 0 | 0 | 0 | 0 |
|  | 1.5 | 0 | 0 | 0 | 0 | 0 | 0 | 0 | 0 | 0 | 0 | 0 | 0 | 0 | 0 | 0 | 0 | 0 | 0 |
|  | 2.0 | 0 | 0 | 0 | 0 | 0 | 0 | 0 | 0 | 0 | 0 | 0 | 0 | 0 | 0 | 0 | 0 | 0 | 0 |
| Example 14 | 1.0 | 0 | 0 | 0 | 0 | 0 | 0 | 0 | 0 | 0 | 0 | 0 | 0 | 0 | 0 | 0 | 0 | 0 | 0 |
|  | 1.5 | 0 | 0 | 0 | 0 | 0 | 0 | 0 | 0 | 0 | 0 | 0 | 0 | 0 | 0 | 0 | 0 | 0 | 0 |
|  | 2.0 | 0 | 0 | 0 | 0 | 0 | 0 | 0 | 0 | 0 | 0 | 0 | 0 | 0 | 0 | 0 | 0 | 0 | 0 |

1. = 1 month after sowing
2. = treatment at the time of stooling
3. = treatment during blooming

EXAMPLE 4

The activity of the test formulations against powdery mildew (Erysiphe graminis f.sp.tritici):

The activity of the test formulations against powdery mildew (Erysiphe graminis f.sp.tritice) in winter wheat cultures was tested following the method disclosed in "Fungicidal and bactericidal test methods", Mezögazdasági és Élelmezésügyi Minisztérium, Növényvédelmi és Agrok/émiai Központ (1978), Chapter 3.2.01.2.

Into 5 ha. plots winter wheat (variety "Száva") was sown in an amount of 380 kg./ha.

The test formulations were applied to the area in a dose of 1.5 kg./ha. as tank mixture, in an amount of 80 lit./ha. Treatments were carried out at the end of stooling and at the end of blooming by helicopter. The evaluation was carried out on one hundred plants and tests were performed in four repetitions. The results obtained separately on four levels of leaves were averaged and the weight of thousand seeds and the "hectoliter weight" were also determined. The results obtained are given in the following Table.

What we claim is:

1. A process for the preparation of a stable, aqueous suspension of methyl-N-(2-benzimidazolyl)-carbamate in the form of particles of a size less than 5 microns, which comprises the steps of:
   (a) treating an aqueous inorganic acid with carbendazime at a temperature of 100° C. to 50° C. to form an aqueous solution of an inorganic acid addition salt of methyl N-(2-benzimidazolyl)-carbamate and adding a wetting agent to said solution;
   (b) treating the solution at a temperature of 100° C. to 50° C. with an aqueous potassium, sodium or ammonium hydroxide solution or with ammonia gas in the presence of a dispersing agent with stirring to form methyl-N-(2-benzimidazolyl)-carbamate in suspension; and
   (c) thereafter maintaining the resulting suspension at a temperature of about 40° to 60° C. and adding an aqueous solution of an antideposit agent to said suspension.

2. The process defined in claim 1 wherein a protecting colloid is present during the reaction.

3. The process defined in claim 1 wherein the acid in step a is hydrochloric acid or phosphoric acid.

4. The process defined in claim 1 wherein the pH of the solution of the acid addition salt is adjusted to 4 to 9 and the methyl N-(2-benzimidazolyl)-carbamate concentration to 10 to 50% by proper selection of the concentration of the solution to be reacted relative to the methyl N-(2-benzimidazolyl)-carbamate or to hydrogen ion and of the mutual amounts of the solutions.

5. The process defined in claim 4 wherein the methyl N-(2-benzimidazolyl)-carbamate is present in an amount of 20 to 40% by weight.

|  |  | Powdery mildew | | | | | | | | | | Crop yield | | |
|---|---|---|---|---|---|---|---|---|---|---|---|---|---|---|
|  |  | After the 1st treatment Leaf levels | | | | | After the 2nd treatment Leaf levels | | | | | | Weight of 1000 seeds | Hectoliter |
| Treatment | Dose [kg/ha] | 1. I | 2. I | 3. I | 4. I | Mean I. | 1. I | 2. I | 3. I | 4. I | Mean I. | g./ha. | g./1000 pieces | weight kg./hl. |
| Example 14 | 1.5 | — | 0.06 | 0.55 | 0.86 | 0.36 | 1.05 | 0.57 | 1.19 | — | 0.7 | 46.05 | 38.32 | 82.70 |
| ABEM 25 FW (control) | 1.5 | — | — | 0.42 | 1.6 | 0.50 | 1.25 | 1.41 | 1.38 | — | 1.01 | 45.2 | 38.10 | 82.4 |
| Thiovit | 5.0 | — | — | 0.4 | 1.31 | 0.43 | 1.57 | 1.48 | 1.26 | — | 1.08 | 44.3 | 38.10 | 81.2 |
| untreated control | — | — | 0.5 | 1.69 | 2.79 | 1.25 | 1.98 | 2.61 | 2.56 | — | 1.79 | 42.8 | 37.4 | 82.1 |

I = infection index, wherein 0 = no infection, 6 = 76 to 100% infection. The results were determined on the basis of the frequency of the various categories and the total number of the test plants.

6. The process defined in claim 1 which comprises reacting an aqueous solution of an acid addition salt of methyl N-(2-benzimidazolyl)-carbamate with an ammonium hydroxide solution or ammonia gas.

7. The process defined in claim 1 which comprises using lignin sulfonate or urea as a dispersing agent.

8. The process defined in claim 1 which comprises using alkylphenolpolyglycol ether or ethoxylated caster oil as a wetting agent.

9. The process defined in claim 2 which comprises using hydroxyethyl cellulose, polyvinylalcohol or polyvinylpyrrolidone as the protecting colloid.

10. The process defined in claim 1 which comprises using methyl silicate, a mineral oil, or a vegetable oil as an antifoaming agent.

* * * * *